United States Patent
Jones et al.

(10) Patent No.: US 8,818,733 B2
(45) Date of Patent: Aug. 26, 2014

(54) DETERMINATION OF PHOTODYNAMIC THERAPY (PDT) TREATMENT PARAMETERS

(75) Inventors: Linda R. Jones, Mount Pleasant, SC (US); Herbert C. Wolfsen, Ponte Vedra Beach, FL (US); Michael B. Wallace, Ponte Vedra Beach, FL (US); Nathan J. Towles, North Augusta, SC (US); Fletcher B. Moore, Manning, SC (US)

(73) Assignees: Mayo Foundation for Medical Education and Research, Rochester, MN (US); College of Charleston, Charleston, SC (US)

( * ) Notice: Subject to any disclaimer, the term of this patent is extended or adjusted under 35 U.S.C. 154(b) by 602 days.

(21) Appl. No.: 13/090,995

(22) Filed: Apr. 20, 2011

(65) Prior Publication Data

US 2011/0270056 A1  Nov. 3, 2011

Related U.S. Application Data

(60) Provisional application No. 61/325,932, filed on Apr. 20, 2010.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................. 702/19; 702/22; 703/11; 703/12

(58) Field of Classification Search
None
See application file for complete search history.

(56) References Cited

U.S. PATENT DOCUMENTS

| | | | |
|---|---|---|---|
| 5,318,023 A * | 6/1994 | Vari et al. | 600/317 |
| 5,533,508 A | 7/1996 | Doiron | |
| 6,128,525 A | 10/2000 | Zeng et al. | |
| 6,377,842 B1 | 4/2002 | Pogue et al. | |
| 2009/0043296 A1 | 2/2009 | Foster et al. | |
| 2011/0042580 A1 * | 2/2011 | Wilson et al. | 250/458.1 |

FOREIGN PATENT DOCUMENTS

WO  2008/137737 A2  11/2008

OTHER PUBLICATIONS

"Photodynamic Therapy Dosimetry," American Association of Physicists in Medicine, AAPM Report No. 88, Jul. 2005, 36 pp.
Amelink, "Monitoring PDT by means of superficial reflectance spectroscopy," Journal of Photochemistry and Photobiology B: Biology 79, Jan. 24, 2005, pp. 243-251.
Gill, "Pilot Study on Light Dosimetry Variables for Photodynamic Therapy of Barrett's Esophagus with High-Grade Dysplasia," Clinic Cancer Research 2009;15(5), Mar. 1, 2009 (www.aacrjournals.org), pp. 1830-1836.
Aalders, "Photodetection with 5-Aminolevulinic Acid-induced Protoporphyrin IX in the Rat Abdominal Cavity: Drug-dose-dependent Fluorescence Kinetics," Photochemistry and Photobiology 2000, 72(4), pp. 521-525.

(Continued)

*Primary Examiner* — Larry D Riggs, II
(74) *Attorney, Agent, or Firm* — Shumaker & Sieffert, P.A.

(57) ABSTRACT

A photodynamic therapy system and methods determine the amount (concentration) of a photosensitizer agent present in the target tissue. The system may also determine the tissue oxygenation. The system may also determine light dosimetry parameters based on the amount of photosensitizer in the tissue and/or the tissue oxygenation.

20 Claims, 6 Drawing Sheets

(56) References Cited

OTHER PUBLICATIONS

Andersson-Engels, "Preliminary Evaluation of Two Fluorescence Imaging Methods for the Detection and the Delineation of Basal Cell Carcinomas of the Skin," Laser in Surgery and Medicine 2000, 26, pp. 76-82.

Sinaasappel, "Quantification of the hematoporphyrin derivative by fluorescence measurement using dual-wavelength excitation and dual-wavelength detection," Applied Optics, Feb. 1, 1993, vol. 32, No. 4, pp. 541-548.

Lin, "Cystoscopic Fluorescence Detector for Photodetection of Bladder Carcinoma with Hematoporhyrin Derivative," Journal of Urology 1984, vol. 131, pp. 587-590.

* cited by examiner

DETERMINATION OF PHOTODYNAMIC THERAPY (PDT) TREATMENT PARAMETERS

CROSS REFERENCE TO RELATED APPLICATIONS

This application claims priority to U.S. Provisional Application 61/325,932, filed Apr. 20, 2010, which is incorporated herein by reference in its entirety.

STATEMENT REGARDING FEDERALLY SPONSORED RESEARCH OR DEVELOPMENT

This disclosure was made with government support under grant number 1R15CA120106-01A1 awarded by the National Institutes of Health (NIH). The government has certain rights in the invention.

TECHNICAL FIELD

The disclosure relates to photodynamic therapy (PDT).

BACKGROUND

In many circumstances undesirable tissue is removed from internal structures of a patient, for example pre-cancerous or cancerous tissue. Many techniques exist for the removal of undesirable tissue, one example of which is photodynamic therapy (PDT). PDT is a "drug and light" therapy that involves the combined effect of a photosensitizer agent, such as porfimer sodium (Photofrin®), and delivery of laser light to result in ablation of the target tissue.

One challenge in the application of PDT is to predict the effect that PDT will have on a particular patient. While standard doses of drug and light are typically used, the clinical outcomes are quite variable. Some patients have a very aggressive response to treatment. In such cases, PDT applied according to standard recommendations may result in the unintended destruction of healthy tissue. For example, damage to normal tissue from a patient's esophagus can cause severe stricturing of the esophageal lumen that may take numerous endoscopic dilation procedures (or even stent placement) to restore so that the patient can eat and drink and take their medicines by mouth. On the other hand, some patients have a very poor response to treatment when administered the same drug and light dose, and some or all of the target tissue remains despite the time, money and resources spent undergoing PDT.

SUMMARY

In general, the disclosure is directed to systems and/or methods for photodynamic therapy (PDT). The PDT systems and/or methods may determine the amount of photosensitizer agent present in the target tissue. The system may also determine the tissue oxygenation status. The system may also determine light dosimetry parameters based on the amount of photosensitizer in the tissue and/or the tissue oxygenation.

In one example, the disclosure is directed to a method comprising introducing a photosensitizer to target tissue of a patient, illuminating the target tissue with one or more wavelengths suitable for fluorescence excitation of the photosensitizer, detecting total emissions from the target tissue over a wavelength range of interest, the emissions including autofluorescence emissions of the target tissue and fluorescence emissions of the photosensitizer, determining the autofluorescence of the target tissue, generating a corrected photosensitizer emission by subtracting the baseline signal from the total emissions from the target tissue, and determining a photosensitizer content ratio based on the corrected photosensitizer emission and the autofluorescence of the target tissue.

The details of one or more examples are set forth in the accompanying drawings and the description below. Other features and advantages will be apparent from the description and drawings, and from the claims.

DETAILED DESCRIPTION

PDT is an endoscopic treatment used for the ablation of cancerous and pre-cancerous conditions. For example, PDT is often used to treat conditions such as Barrett's esophagus with high grade dysplasia and early esophageal adenocarcinoma or squamous cell carcinoma. Treatment of internal organs may be achieved through the use of endoscopes and fiber optic catheters to deliver light, and intravenously-administered photosensitizers. PDT may also be used to treat other conditions such as skin cancer, macular degeneration, psoriasis, etc.

The present disclosure relates generally to photodynamic therapy systems and/or methods that determine the amount of photosensitizer agent present in the target tissue. The systems/methods may also determine the tissue oxygenation status. The systems/methods may also determine light dosimetry parameters based on the amount of photosensitizer in the tissue and/or the tissue oxygenation.

Figure 1:
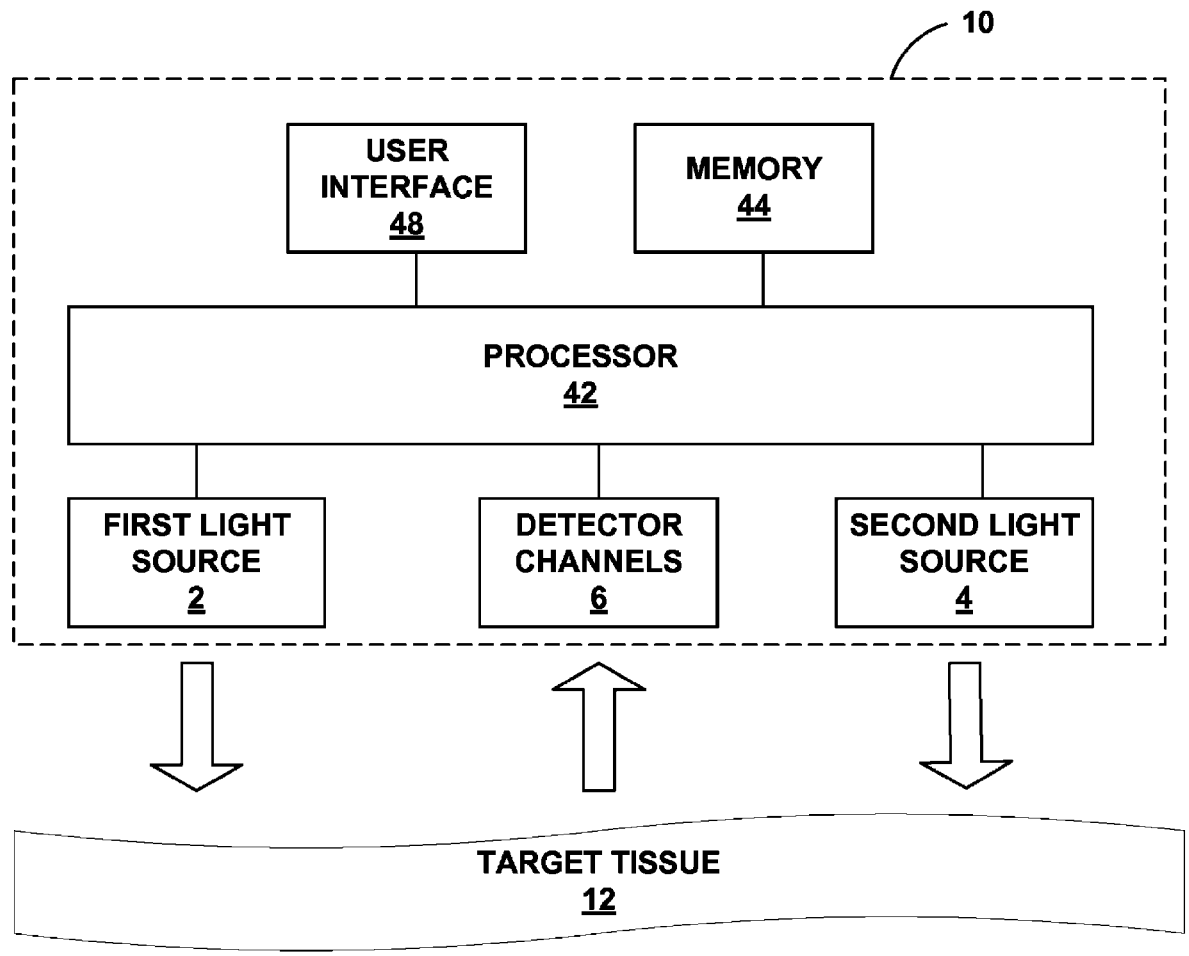
FIG. 1 is a block diagram illustrating an example photodynamic therapy (PDT) system that determines the amount of photosensitizer agent in target tissue of a patient.

FIG. 1 is a block diagram illustrating an example system 10 that determines the concentration of a photosensitizing agent in target tissue 12 of a patient. System 10 may also determine the tissue oxygenation of the target tissue 12 and/or determine light dosimetry parameters based on the concentration of photosensitizing agent and/or the tissue oxygenation. Example system 10 includes a first light source 2, a second light source 4, and one or more detector channels 6. System 10 also includes a processor 42, a user interface 48, and a memory 44. The hardware of example system 10 may be implemented using the Jaz Modular Optical Sensing Suite available from Ocean Optics, Inc, Dunedin, Fla. (www-.oceanoptics.com). However, it shall be understood that custom or other off the shelf hardware implementations may also be used, and that the disclosure is not limited in this respect.

Figure 2A:
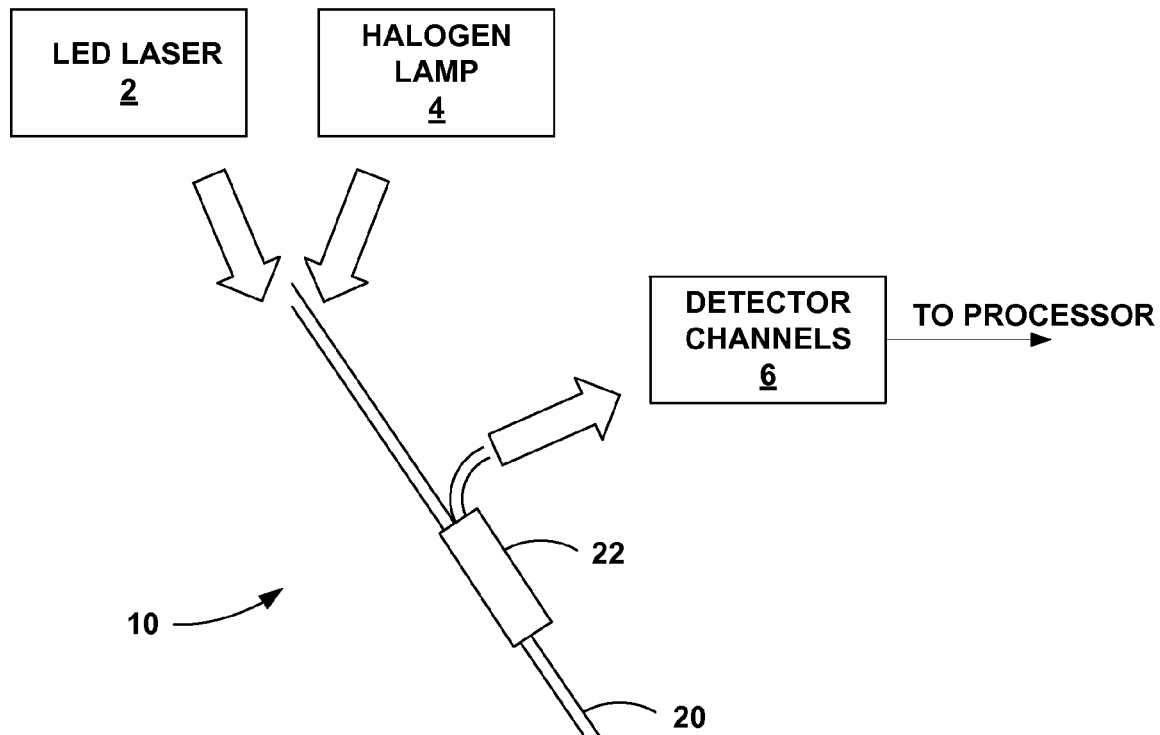
FIGS. 2A and 2B are schematic diagrams illustrating an example PDT system that determines the amount of photosensitizer agent in target tissue.

FIG. 2A is a schematic diagram of portions of system 10. In this example, treatment of internal organs, such as the esophagus, is achieved through the use of a fiber optic catheter 22 (shown cut away) to deliver the light to the target tissue 12. In this example, light sources 2 and 4 may include an LED laser having a wavelength of approximately 405 nanometers (nm) and a halogen lamp, respectively. LED laser 2 provides fluorescence excitation at the peak absorption of the photosensitizer. In this example, the photosensitizer is porfimer sodium. The halogen lamp provides white light for full spectrum diffuse reflectance from target tissue 12. It shall be understood that other light sources having appropriate excitation wavelengths could also be used depending upon the particular photosensitizer(s) present in the target tissue.

Figure 2B:
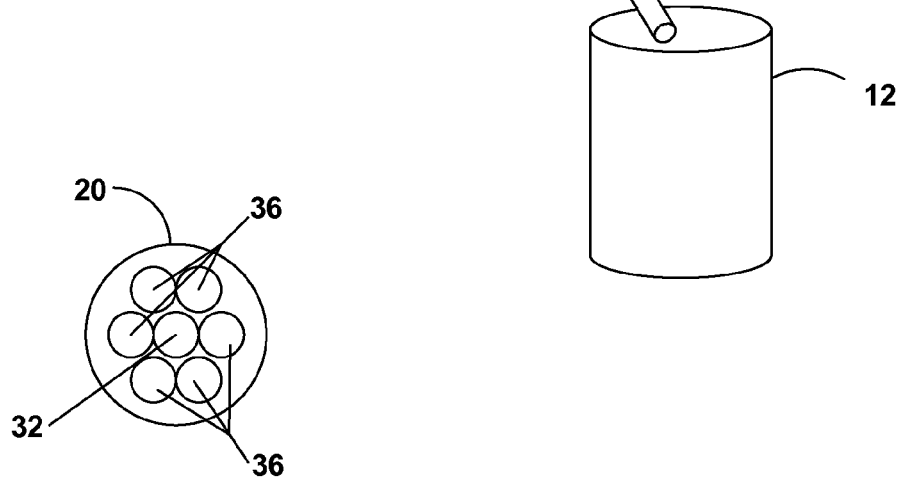

Light from the LED laser 2 and halogen lamp 4 are delivered to the target tissue 12 (one at a time) via a fiber optic bundle 20. FIG. 2B is a cross-sectional view of an example fiber optic bundle 20. In this example, fiber optic bundle 20 includes a central illumination fiber 32 surrounded by six detection fibers 36. However, it shall be understood that any appropriate light transmitting connector could be used in place of fiber optic bundle 20, and that the disclosure is not limited in this respect.

Many photosensitizing agents are fluorescent substances. That is, when the photosensitizing agent is illuminated with light of an appropriate incident wavelength, the photosensitizing agent produces a fluorescent emission at one or more different wavelengths. For example, porfimer sodium, when illuminated with an LED laser having a wavelength of approximately 405 nm, will produce fluorescence emissions having wavelengths in the range of approximately 605 nm to 750 nm. Other photosensitizing agents may have the same or different wavelengths for fluorescent excitation or produce fluorescence emissions at the same or different wavelengths.

Detector 6 may be configured to detect the diffuse reflectance of the tissue of the light from the halogen lamp, the fluorescence emissions of the photosensitizing agent present in the tissue, and/or the autofluorescence of the tissue. To that end, detector 6 may include one or more channels corresponding to the one or more wavelengths to be detected. The reflected light, the fluorescence emissions of the photosensitizing agent, and/or the autofluorescence emissions of the tissue are received by processor 42 (FIG. 1) from detector 6.

Processor 42 analyzes the reflectance, fluorescence, and/or autofluorescence emissions as discussed in further detail herein to determine the amount of the photosensitizing agent in the tissue. Processor 42 may also determine the tissue oxygenation and/or light dosimetry parameters.

Examples of photosensitizer agents include porphyrins, chlorophylls, and dyes. Specific examples of photosensitizers include aminolevulinic acid (ALA), silicon phthalocyanine Pc 4, m-tetrahydroxyphenylchlorin (mTHPC), mono-L-aspartyl chlorin e6 (NPe6). Other examples include photosensitizers known by the commercial names Photofrin® (porfimer sodium), Visudyne®, Levulan®, Foscan®, Metvix®, Hexvix®, Laserphyrin®, Antrin®, Photochlor®, Photosens®, Aptocine™, and/or BF-200 ALA. It shall be understood, however, that these are merely examples of photosensitizers, and that other photosensitizers may also be applicable to the present disclosure, and that the disclosure is not limited in this respect.

The one or more photosensitizers may be introduced to the target tissue via one or more techniques known in the art, including intravenous injection, subcutaneous injection, intramuscular injection, topical application, orally and/or other means of introducing a photosensitizer into the target tissue. Although several example means for introducing a photosensitizer into target tissue are described herein, it shall be understood that any appropriate means of introducing the photosensitizer agent into the target tissue may be used, and that the disclosure is not limited in this respect.

Detector 6 may operate in conjunction with one or more fiber-optic elements, such as fiber-optic cables, to transmit the diffuse reflectance of the tissue, the autofluorescence emissions of the tissue and/or the fluorescence emissions of the photosensitizer agent from the target tissue 12 to detector 6. In one example, detector 6 and light elements 2 and 4 may share one or more fiber-optic elements. In other examples, separate fiber-optic elements may be provided for detector 6 and light elements 2 and 4.

Detector 6 may operate in conjunction with one or more optical structures (e.g., lens, waveguide, beam-splitter, optical amplifier/pre-amplifier, lock-in amplifier, and one or more electrical components to measure characteristics of received electromagnetic energy. For example, detector 6 may include one or more filters or waveguides configured to distinguish between specific wavelengths of electromagnetic energy. In one example, detector 6 may be one or more transducers configured to translate received electromagnetic energy, e.g., light, into one or more electrical signals for further processing.

Processor 42 may be implemented using one or more microprocessors, micro-controllers, CPUs, or other signal processing components configured to process, interpret and/or analyze the reflectance, autofluorescence or fluorescence emissions detected by detector 6. User interface 48 may receive various commands from a user and/or present the detected, processed, and/or analyzed data to a user, such as a physician.

In one example, the above-described components may be implemented in a hand-held unit. The hand-held unit may house light sources 2 and 4 and detector 6. The hand-held unit may further include the above-described optical and electrical processing, display, and/or analysis components. The hand-held unit may further incorporate one or more displays, and or one or more user input mechanisms, to enable communication with a user regarding detected results and/or suggestions for PDT therapy.

To determine the relationship between fluorescence emissions of the photosensitizer and the amount (concentration) of photosensitizer in the tissue, experiments were conducted using tissue phantoms. Tissue phantoms were constructed of intralipid, saline, and bovine blood. Porfimer sodium was added in concentrations from 2 to 10 mg/kg.

Figure 3:
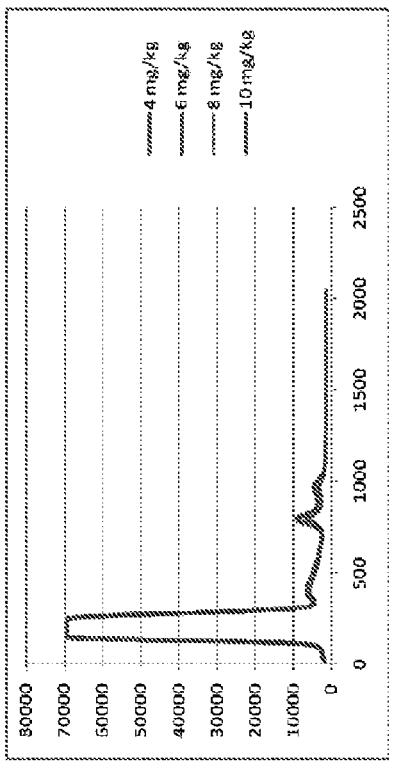
FIG. 3 shows a graph of fluorescence emission vs. wavelength for a tissue phantom.

FIG. 3 is a graph of fluorescence emission intensity vs. wavelength (between 0 and 2000 nm) for various known concentrations of porfimer sodium in a tissue phantom. The peak around 405 nm is the reflected excitation laser light.

Figure 4:
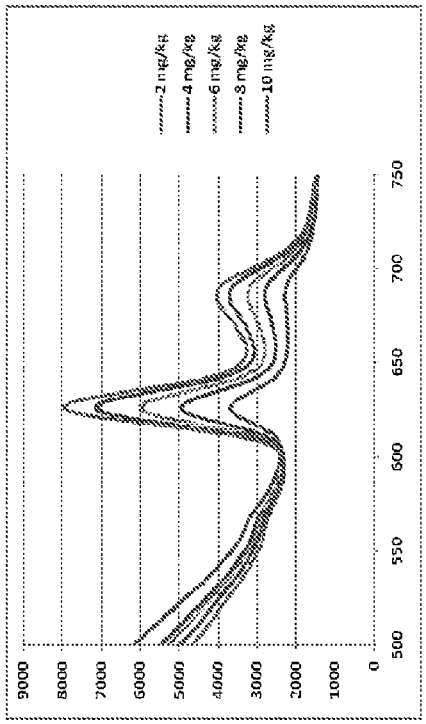
FIG. 4 shows a graph of fluorescence emission vs. wavelength for various concentrations of porfimer sodium in a tissue phantom.

FIG. 4 is a graph of fluorescence emission intensity vs. wavelength (between 500 and 750 nm) for various known concentrations (2 mg/kg, 4 mg/kg, 6 mg/kg, 8 mg/kg and 10 mg/kg) of porfimer sodium in a tissue phantom. The spectrum below 600 nm represents autofluorescence of the tissue, similar to that found in biological tissues. The spectrum above 600 nm is a combination of autofluorescence and porfimer sodium fluorescence. The large peak around 400 nm is the laser excitation light reflected from the phantom.

To determine porfimer sodium content of the tissue, the fluorescence emission of the porfimer sodium is isolated from the autofluorescence of the tissue. In the porfimer sodium example, the fluorescence emissions of porfimer sodium are generally above 600 nm. Thus, the spectrum below 600 nm may be considered to represent the autofluorescence of the tissue. As shown in FIG. 4, the autofluorescence portion of the spectrum may be generally represented as a straight line to determine the contribution in intensity from autofluorescence between 605 and 720 nm. The autofluorescence may be subtracted point by point (e.g., wavelength by wavelength) from the total fluorescence emission between 605 nm to 720 nm to give a corrected porfimer sodium emission (that is, the total emission less the autofluorescence emission). The integral of the corrected porfimer sodium emission may be found by summing the intensity for each wavelength from 605 nm to 720 nm.

"Background" emissions may be identified as the intensity value sampled at a wavelength where the emission spectra levels out. In this example, the background is sampled at approximately 750 nm. This is the approximate wavelength at which the example porfimer sodium emission spectra levels out (see, e.g., FIG. 4). However, the background may be sampled at any appropriate wavelength, or at multiple wavelengths. The background may then be subtracted from each point (wavelength) in the autofluorescence region between 520 nm and 580 nm to obtain a background corrected autofluorescence. The integral of the background corrected autofluorescence may be found by summing the background compensated intensity values from 520 nm to 580 nm.

Next, a so-called photosensitizer content ratio may be calculated by dividing the corrected porfimer sodium integral by the corrected autofluorescence integral. This ratio corrects for the intensity of the laser because the autofluorescence is proportional to the laser intensity. Therefore, in this example, a separate standardization for intensity is not necessary.

Figure 5:
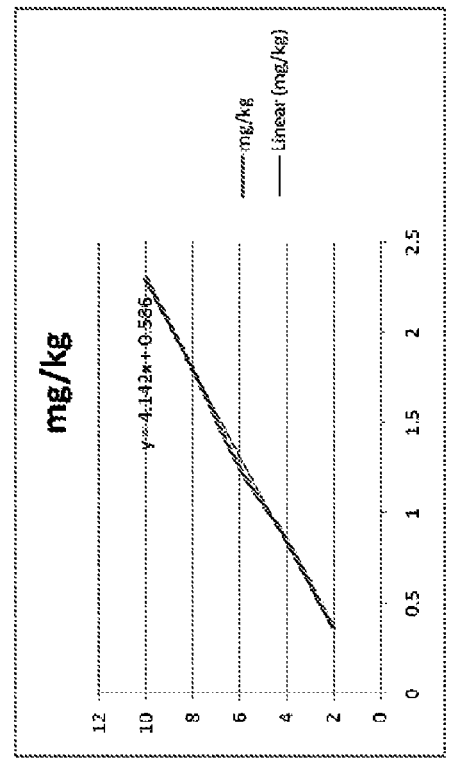
FIG. 5 shows a graph of known concentrations of porfimer sodium in the tissue phantom as a function of the ratio of integrated porfimer sodium fluorescence to integrated autofluorescence emission.

FIG. 5 shows a graph of known concentrations of porfimer sodium in a tissue phantom as a function of the ratio of the corrected porfimer sodium integral to the background corrected autofluorescence integral. FIG. 5 shows a substantially linear relationship between the calculated fluorescence ratio and the known tissue phantom porfimer sodium concentration. It has been found that the slope is independent of incident intensity of the laser. This is because the intensity of the laser is factored out when calculating the photosensitizer content ratio. The slope is also independent of the distance from optical fiber to tissue surface. This distance is also factored out when calculating the photosensitizer content ratio. This may be an advantage because it is usually difficult to control the fiber-tissue distance in the esophagus.

Once the relationship between photosensitizer content and the ratio is determined, a lookup table or other data structure may be generated using the photosensitizer content and the corresponding photosensitizer content ratio. This lookup table may be stored in a memory or other storage device, such as memory 44 of system 10 (FIG. 1). During use, the system may determine the ratio of the corrected porfimer sodium integral to the corrected autofluorescence integral and use that as an index to determine the photosensitizer concentration in the target tissue. Alternatively, an equation for determining photosensitizer content based on the ratio of the corrected porfimer sodium integral to the corrected autofluorescence integral may be determined and used to calculate the photosensitizer concentration in the target tissue.

Figure 6A:
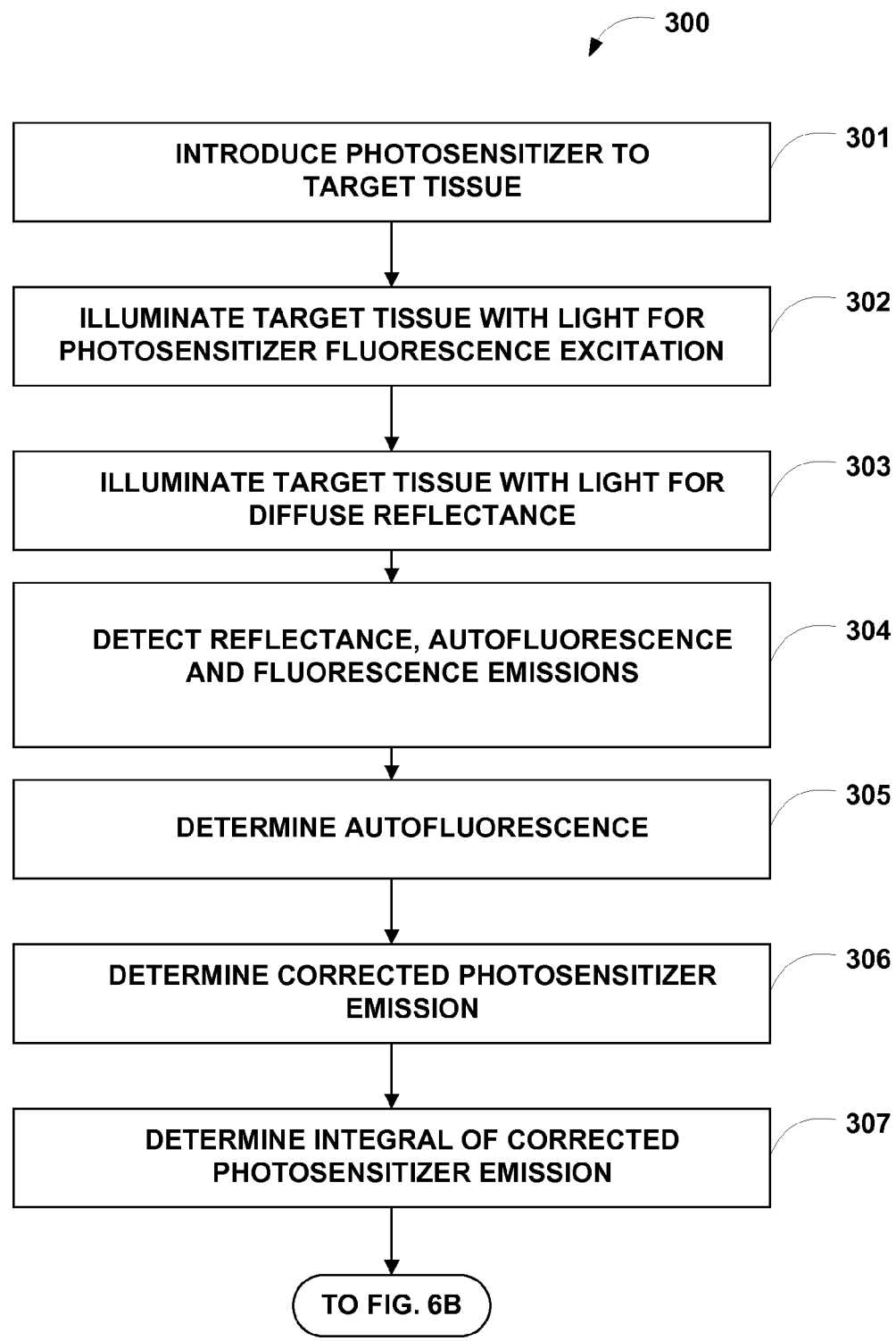
FIGS. 6A-6B are a flowchart illustrating an example process by which a processor may determine the amount of photosensitizer agent in target tissue.
Figure 6B:
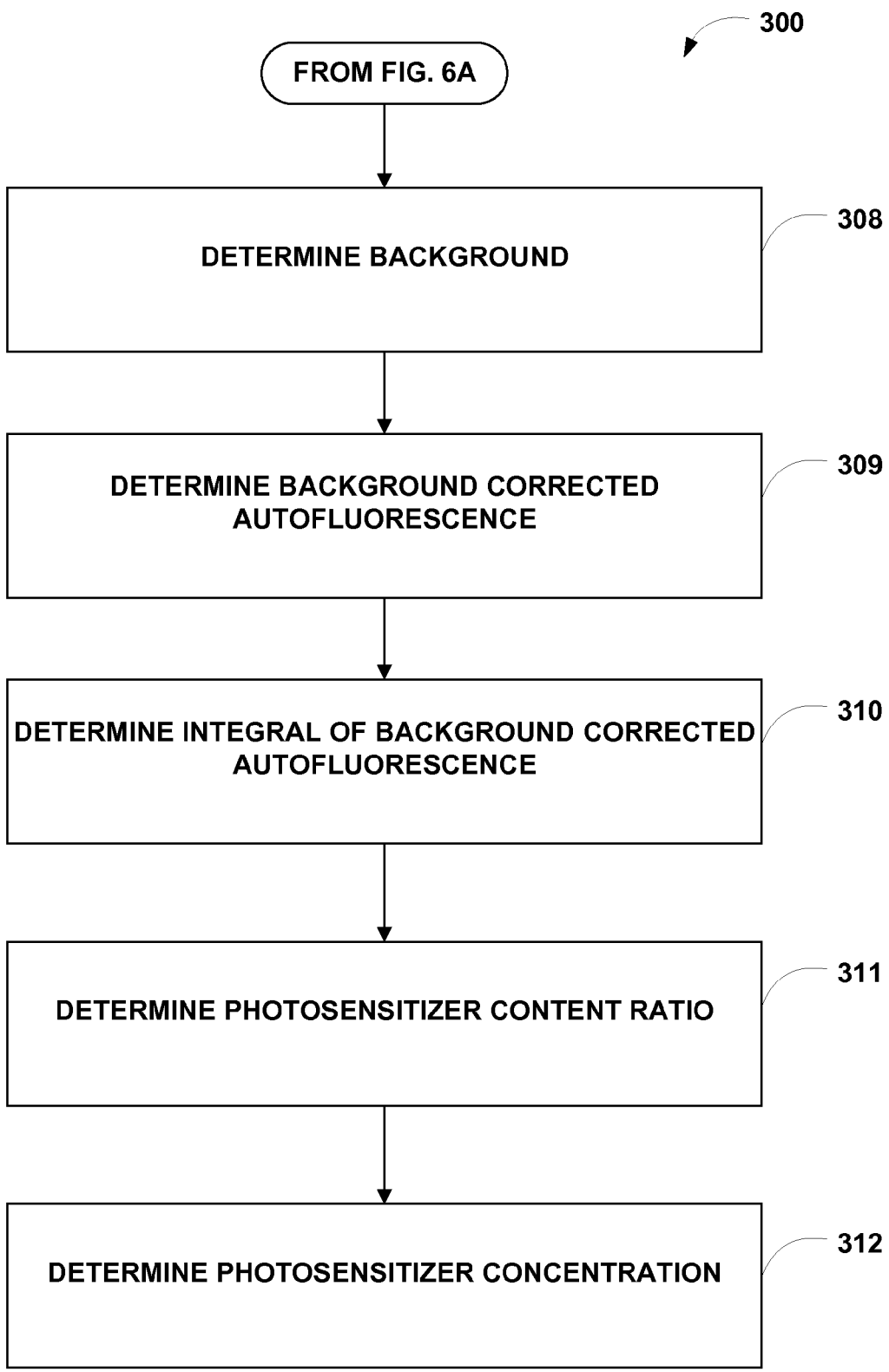

FIGS. 6A-6B are a flowchart illustrating an example process by which a processor may determine the amount of photosensitizer agent in target tissue (300). One or more photosensitizers are first introduced to the target tissue (301). The target tissue is illuminated with light having wavelength (s) suitable for exciting the photosensitizer (302). For example, where the photosensitizer is porfimer sodium, the target tissue may be illuminated using an LED laser having a wavelength of approximately 405 nm. The fluorescence emissions resulting from this illumination may be used to determine the photosensitizer content in the tissue.

The target tissue 12 may also be illuminated with light for purposes of diffuse reflectance (303). For example, the target tissue may be illuminated using a full spectrum (white light) halogen lamp. The reflectance emissions resulting from this illumination may be used to determine the tissue oxygenation.

One or more detectors detect the reflectance, autofluorescence and fluorescence emissions resulting from illumination with the light for photosensitizer excitation (304). Once the spectrum is obtained, the autofluorescence of the tissue is determined (305). This may be accomplished as described above for the porfimer sodium example, and similarly for other photosensitizers, by determining the mathematical relationship between the autofluorescence and wavelength between approximately 520-580 nm (or the autofluorescence range relevant to the particular photosensitizer/excitation wavelength at issue), then extrapolating that relationship to the wavelengths between approximately 605-720 nm (or between the photosensitizer fluorescence range relevant to the particular photosensitizer/excitation wavelength at issue)

A corrected photosensitizer emission is determined (306). In the porfimer sodium example (and similarly for other photosensitizers), the autofluorescence may be subtracted point by point (e.g., wavelength by wavelength) from the total fluorescence emission between 605 nm to 720 nm (or between the wavelengths relevant to the particular photosensitizer/excitation wavelength at issue) to give a corrected porfimer sodium emission (that is, the total emission less the autofluorescence emission). The integral of the corrected porfimer sodium emission may be found by summing the intensity over the desired wavelength range (307) (for each wavelength from 605 nm to 720 nm in the porfimer sodium example).

In this example, the autofluorescence (305) is estimated as a straight line fitted between 605 nm and 720 nm:

$$y(\lambda)=mx+b,$$

where $m=[I(720\text{ nm})-I(605\text{ nm})]/(720\text{ nm}-605\text{ nm})$ $b=I(720\text{ nm})-m*720.$ This is subtracted point by point from the porfimer sodium fluorescence emission to give the autofluorescence-corrected porfimer sodium emission:

$$I(\lambda, \text{autofluorescence corrected})=I(\lambda)-y(\lambda).$$

Emissions due to background noise may also be determined (308). In the porfimer sodium example, the intensity of the background emission may sampled at approximately 750 nm or other appropriate wavelength. For other photosensitizers, the background may be sampled at any relevant wavelength where fluorescence emission spectra levels out. The background may then be subtracted from each point (wavelength) in the autofluorescence region between 520 nm and 580 nm (or other relevant wavelength, depending upon the particular photosensitizer/excitation wavelength at issue) to obtain a background corrected autofluorescence (309). It is also subtracted from each point (wavelength) in the photosensitizer fluorescence region from 605 nm to 750 nm (or other relevant wavelength) to give the background-corrected photosensitizer fluorescence:

$$I(\lambda, \text{background-corrected})=I(\lambda)-I(750\text{ nm}).$$

The integral of porfimer sodium emission (307) is found by summing the intensity for each point from 605 nm to 720 nm:

Photosensitizer Integral=Sum[*I*(background-corrected)from 605 to 720 nm].

The integral of the background corrected autofluorescence (310) may be found by summing the background compensated intensity values from 520 nm to 580 nm (or other relevant wavelength, depending upon the particular photosensitizer/excitation wavelength at issue):

Autofluorescence integral=Sum[*I*(λ,background-corrected)] from 520 nm to 580 nm.

In this example, the processor also calculates a so-called photosensitizer content ratio (311). This may be accomplished as described above with respect to the porfimer sodium example by dividing the corrected porfimer sodium integral by the corrected autofluorescence integral:

Photosensitizer Content Ratio=Photosensitizer integral/Autofluorescence integral.

Figure 7:
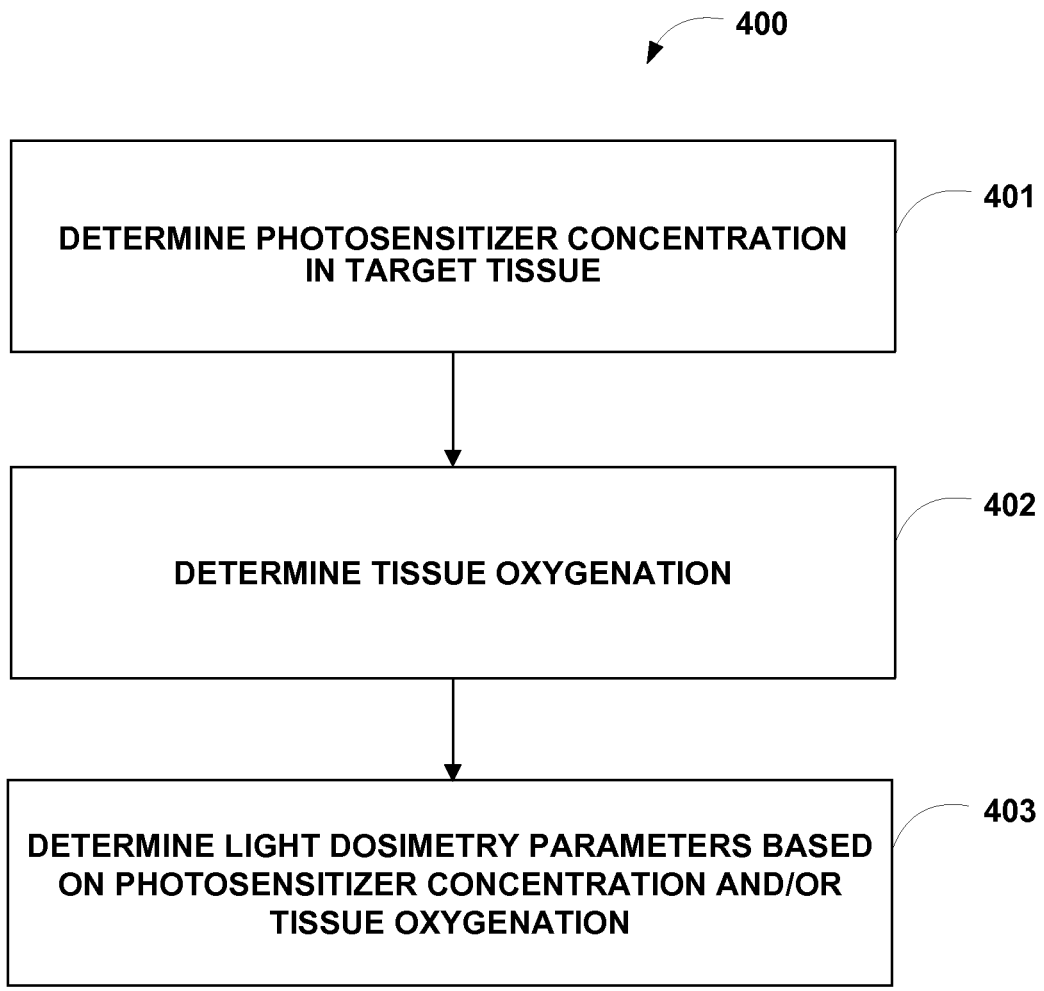
FIG. 7 is a flowchart illustrating an example process by which a processor may determine light dosimetry parameters based on the amount of photosensitizer agent in the target tissue and the tissue oxygenation.

As shown in FIG. 7, the processor may then use the photosensitizer content ratio to determine the actual amount (concentration) of photosensitizer present in the target tissue (401). As depicted in FIG. 5, the photosensitizer content ratio may define a linear relationship with the actual photosensitizer concentration in the target tissue. The system may store a look-up table or other data structure which permits the processor to index the photosensitizer content ratio and arrive at the actual photosensitizer concentration. Alternatively, the system may store an equation describing the relationship between the photosensitizer content ratio and the actual photosensitizer concentration.

FIG. 7 is a flowchart illustrating an example process by which a processor may determine one or more light dosimetry parameters based on the amount of photosensitizer agent in the target tissue and the tissue oxygenation. The example process shown in FIG. 7 includes determining a photosensitizer concentration in target tissue (401). For example, photosensitizer concentration in the target tissue may be determined according to the process shown in FIGS. 6A-6B.

The tissue oxygenation of the target tissue may also be determined (402). Various techniques are known in the art for determining the tissue oxygenation. One such technique is described in A. Amelink et al., "*Monitoring PDT by Means of Superficial Reflectance Spectroscopy*," Journal of Photochemistry and Photobiology B: Biology 79 (2005), pp. 243-251, which is incorporated by reference herein in its entirety. This technique involves a spreadsheet technique for determining the tissue oxygenation (blood volume by percent and hemoglobin oxygen saturation) based on the diffuse reflectance of the tissue.

The process may also include determining light dosimetry parameters based on the photosensitizer concentration in the target tissue and/or the tissue oxygenation (403). For example, various light dosimetry parameters may be determined, including incident light intensity, exposure time, fractionation of light dose, etc.

One example of a determination of light dosimetry parameters based on photosensitizer content (but not tissue oxygenation) may be found in Gill, et al., "*Pilot Study on Light Dosimetry Variables for Photodynamic Therapy of Barrett's Esophagus with High Grade Dysplasia*", Clin Cancer Research 2009; 15(5) Mar. 1, 2009 (www.aacrjournals.org). In that example, two different forms of photodynamic dose were calculated. The first form was a product of administered light dose in units of J/cm and the photosensitizer (porfimer sodium) tissue content in mg/kg as given in the following equation:

*PDT* Dose=[porfimer sodium]*light dose.

A second form of photodynamic dose incorporated the variable of esophageal thickness:

Enhanced *PDT* Dose=[porfimer sodium]*light dose*(1/total esophageal thickness).

In another example, the process (403) may determine light dosimetry parameters based on the photosensitizer concentration in the target tissue and the tissue oxygenation.

In some examples, the photosensitizer concentration may be compared to one or more threshold concentrations. For example, if the photosensitizer concentration is less than a first threshold concentration, additional photosensitizer may be introduced to the target tissue to improve the effects of the PDT when delivered. As another example, if the photosensitizer concentration is greater than a second threshold concentration, delivery of PDT may be delayed for a period of time such that at least some of the photosensitizer is dissipated from the target tissue. As another example, if the photosensitizer concentration is less than a third threshold concentration, the light dose (intensity and/or duration) may be adjusted to improve the effects of the PDT when delivered. The one or more threshold concentrations may be the same or different.

Referring again to FIG. 1, processor 42 may be configured to analyze results of one or both of the methods depicted in FIGS. 6A-6B and 7, and may automatically provide one or more recommendations for PDT delivery to a user. For example, the processor may be configured to compare the results of one or more of the methods described above to one or more predefined thresholds, and provide a user with light dosimetry parameters for the delivery of PDT based on the comparison(s) via user interface 48.

In one example, the system 10 may be configured to, in addition to determining photosensitizer content, tissue oxygenation, and/or associated recommendations for PDT parameters, perform the PDT itself. Thus, the system may be configured to automatically determine parameters for delivery of PDT, and deliver the PDT without little or no operator (physician) intervention.

In another example, the system may modify a PDT therapy in real-time during application of the PDT. For example, as the device illuminates target tissue 12 to stimulate photosensitizer in the tissue, the device may calculate the photosensitizer content in the tissue according to the method of FIG. 6. The device may also determine tissue oxygenation as described with respect to FIG. 7. Based on one or more of these determinations, the unitary hand-held device may adjust (or enable user adjustment of) a delivered therapy in real-time, for example by modifying an intensity of light that illuminates target tissue, modifying a location of target tissue illuminated, and/or modify a duration of illumination.

One or more of the techniques described herein may be partially or wholly executed in software. For example, a computer-readable medium may store or otherwise comprise computer-readable instructions, i.e., program code that can be executed by a computer or processor to carry out one of more of the techniques described above.

In one example, an implementation may include one or more computer-readable media comprising instructions that cause a processor to carry out the methods described above. A "computer-readable medium" includes but is not limited to read-only memory (ROM), random access memory (RAM), non-volatile random access memory (NVRAM), electrically erasable programmable read-only memory (EEPROM), flash memory, a magnetic hard drive, a magnetic disk or a magnetic tape, a optical disk or magneto-optic disk, CD, CD-ROM, DVD, a holographic medium, or the like. The instructions may be implemented as one or more software modules, which may be executed by themselves or in combination with other software.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet. The connections may be wired or wireless.

As another example, one or more devices that include logic circuitry may carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

Various examples have been described. These and other examples are within the scope of the following claims.

The invention claimed is:

1. A method comprising:
   illuminating target tissue of a patient containing a concentration of a photosensitizer with one or more wavelengths suitable for fluorescence excitation of the photosensitizer;
   detecting total emissions from the target tissue over a wavelength range of interest, the emissions including autofluorescence emissions of the target tissue and fluorescence emissions of the photosensitizer;
   determining the autofluorescence of the target tissue;
   generating a corrected photosensitizer emission by subtracting the autofluorescence emission from the total emissions from the target tissue;
   determining a photosensitizer content ratio based on the corrected photosensitizer emission and the autofluorescence of the target tissue; and
   determining the concentration of the photosensitizer in the target tissue based on the photosensitizer content ratio.

2. The method of claim 1, wherein determining the autofluorescence of the target tissue comprises:
   determining the autofluorescence of the target tissue over a first subset of the wavelength range of interest; and
   determining the autofluorescence of the target tissue over a second subset of the wavelength range of interest based on the autofluorescence of the target tissue over a first subset of the wavelength range of interest.

3. The method of claim 1, further comprising:
   determining a background emission; and
   generating a corrected autofluorescence by subtracting the background emission from the autofluorescence emission.

4. The method of claim 1, wherein determining the concentration of the photosensitizer in the target tissue based on the photosensitizer content ratio comprises calculating the concentration of the photosensitizer in the target tissue using an equation that describes the relationship between the photosensitizer content ratio and the concentration of the photosensitizer in the target tissue.

5. The method of claim 1, wherein determining the concentration of the photosensitizer in the target tissue based on the photosensitizer content ratio comprises determining the concentration of the photosensitizer in the target tissue using a lookup table that indexes the photosensitizer content ratio and the concentration of the photosensitizer in the target tissue.

6. The method of claim 1 further comprising determining the tissue oxygenation of the target tissue based on the diffuse reflectance of the tissue.

7. The method of claim 1 further comprising determining light dosimetry parameters based on the photosensitizer concentration in the target tissue.

8. The method of claim 7 wherein determining light dosimetry parameters comprises determining one or more of incident light intensity, exposure time, and fractionation of light dose.

9. The method of claim 1 further comprising determining light dosimetry parameters based on the photosensitizer concentration in the target tissue and the tissue oxygenation.

10. The method of claim 1 further comprising comparing the concentration of the photosensitizer to one or more threshold concentrations.

11. The method of claim 1 further comprising comparing the concentration of the photosensitizer to a threshold concentration and introducing additional photosensitizer to the target tissue if the concentration of the photosensitizer is less than a threshold concentration.

12. The method of claim 1 further comprising comparing the concentration of the photosensitizer to a threshold concentration delaying delivery of photodynamic therapy if the concentration of the photosensitizer is greater than the threshold concentration.

13. The method of claim 1 further comprising comparing the concentration of the photosensitizer to a threshold concentration and adjusting a photodynamic therapy light dose if the concentration of the photosensitizer is less than the threshold concentration.

14. The method of claim 1 further comprising automatically providing one or more recommendations for photodynamic therapy based on one or more of the concentration of the photosensitizer.

15. The method of claim 1 further comprising modifying application of a photodynamic therapy based on one or more of the concentration of the photosensitizer in the target tissue and the tissue oxygenation.

16. The method of claim 15, wherein modifying application of a photodynamic therapy comprising one or more of modifying an intensity of a photodynamic therapy light dose, modifying a location of target tissue exposed to the photodynamic therapy light dose, and modifying a duration of the photodynamic therapy light dose.

17. A non-transitory computer readable medium comprising instructions that cause a processor to:
   control illumination of target tissue of a patient containing a concentration of a photosensitizer with one or more wavelengths suitable for fluorescence excitation of the photosensitizer;
   receive total emissions from the target tissue over a wavelength range of interest, the emissions including autofluorescence emissions of the target tissue and fluorescence emissions of the photosensitizer;
   determine the autofluorescence of the target tissue;
   generate a corrected photosensitizer emission by subtracting the autofluorescence emission from the total emissions from the target tissue;
   determine a photosensitizer content ratio based on the corrected photosensitizer emission and the autofluorescence of the target tissue; and
   determine the concentration of the photosensitizer in the target tissue based on the photosensitizer content ratio.

18. A system, comprising:
a light source that illuminates target tissue of a patient containing a concentration of a photosensitizer with one or more wavelengths suitable for fluorescence excitation of the photosensitizer;
one or more detectors that detect total emissions from the target tissue over a wavelength range of interest, the emissions including autofluorescence emissions of the target tissue and fluorescence emissions of the photosensitizer; and
a processor that receives the autofluorescence emissions and the total emissions, determines the autofluorescence of the target tissue, generates a corrected photosensitizer emission by subtracting the autofluorescence emission from the total emissions from the target tissue, determines a photosensitizer content ratio based on the corrected photosensitizer emission and the autofluorescence of the target tissue, and determines the concentration of the photosensitizer in the target tissue based on the photosensitizer content ratio.

19. The system of claim 18 wherein the processor calculates the concentration of the photosensitizer in the target tissue using an equation that describes the relationship between the photosensitizer content ratio and the concentration of the photosensitizer in the target tissue to determine the concentration of the photosensitizer in the target tissue.

20. The system of claim 18 wherein the processor refers to a lookup table that indexes the photosensitizer content ratio and the concentration of the photosensitizer in the target tissue to determine the concentration of the photosensitizer in the target tissue.

\* \* \* \* \*